(12) United States Patent
Klein et al.

(10) Patent No.: US 8,040,132 B2
(45) Date of Patent: Oct. 18, 2011

(54) METHOD FOR IDENTIFYING A SAMPLE IN A CONTAINER, E.G. WHEN CONDUCTING A TRAVELER SURVEY IN THE CHECK-IN AREA, BY DETERMINING THE RESONANCE FREQUENCY AND THE QUALITY OF A DIELECTRIC RESONATOR TO WHICH THE CONTAINER IS ARRANGED

(75) Inventors: Norbert Klein, Juelich (DE);
Hans-Joachim Krause, Baesweiler (DE); Willi Zander, Aldenhoven (DE)

(73) Assignee: Forschungszentrum Juelich GmbH, Juelich (DE)

( * ) Notice: Subject to any disclaimer, the term of this patent is extended or adjusted under 35 U.S.C. 154(b) by 296 days.

(21) Appl. No.: 12/311,238

(22) PCT Filed: Sep. 24, 2007

(86) PCT No.: PCT/DE2007/001712
§ 371 (c)(1),
(2), (4) Date: Mar. 23, 2009

(87) PCT Pub. No.: WO2008/040305
PCT Pub. Date: Apr. 10, 2008

(65) Prior Publication Data
US 2010/0026300 A1 Feb. 4, 2010

(30) Foreign Application Priority Data
Sep. 29, 2006 (DE) .................. 10 2006 046 657
Mar. 22, 2007 (DE) .................. 10 2007 014 492

(51) Int. Cl.
*G01V 3/00* (2006.01)

(52) U.S. Cl. ............. 324/308; 324/307; 324/321
(58) Field of Classification Search ......... 324/300–322; 600/410–435
See application file for complete search history.

(56) References Cited

U.S. PATENT DOCUMENTS
3,443,209 A * 5/1969 Anderson et al. ............. 324/320
(Continued)

FOREIGN PATENT DOCUMENTS
DE 25 52 954 6/1977
(Continued)

OTHER PUBLICATIONS

"Ein Dielektrizitaetskonstanten-Messplatz zur Untersuchung optischer Kristalle im Mikrowellenbereich ( A dielectri constant measuring station for the analysis of optical crystals in the microwave rante)" in: Kristall und Technik, vol. 10, No. 6, 1975, pp. 695-770, by E. Wehrsdorfer et al. E. Wehrsdorfer et al. 10 695-770.

(Continued)

*Primary Examiner* — Dixomara Vargas
(74) *Attorney, Agent, or Firm* — Jordan and Hamburg LLP (57) ABSTRACT

A method and apparatus for identifying a sample in a container, provide for the container with the sample being disposed relative to a resonator, a high-frequency signal being coupled into the resonator for exciting a resonant mode of the resonator, the resonant electric field of the resonator penetrating part of the sample in the container, the resonance curve of at least one resonant mode being measured with and without the sample, and the sample being identified based on the determined change in the resonance frequency compared to a measurement without sample.

42 Claims, 6 Drawing Sheets

U.S. PATENT DOCUMENTS

| | | | |
|---|---|---|---|
| 4,155,035 | A | 5/1979 | Fitzky |
| 5,500,599 | A | 3/1996 | Stange |
| 5,530,350 | A * | 6/1996 | Dechene et al. ............. 324/306 |
| 5,596,275 | A * | 1/1997 | Dechene et al. ............. 324/307 |
| 7,366,560 | B2 * | 4/2008 | Taicher et al. ................ 600/410 |
| 7,379,819 | B2 * | 5/2008 | Betancourt et al. ............ 702/11 |
| 7,423,435 | B2 | 9/2008 | Sawamoto et al. |
| 7,733,490 | B2 * | 6/2010 | Goodwin et al. ............. 356/436 |
| 7,874,355 | B2 * | 1/2011 | O'Keefe et al. ................ 166/173 |
| 2002/0050828 | A1 | 5/2002 | Seward, IV et al. |
| 2007/0000503 | A1 | 1/2007 | Herrmann et al. |

FOREIGN PATENT DOCUMENTS

| | | |
|---|---|---|
| DE | 40 04 119 | 8/1991 |
| DE | 42 04 369 | 9/1993 |
| DE | 43 42 505 | 4/1995 |
| DE | 20 2004 007013 | 7/2004 |
| EP | 0 547 968 | 6/1993 |
| EP | 0 607 558 | 7/1994 |
| EP | 1 321 564 | 6/2003 |
| EP | 1 734 361 | 12/2006 |
| EP | 1 739 411 | 1/2007 |
| GB | 595720 | 12/1947 |
| WO | WO-00/28615 | 5/2000 |
| WO | WO-03/031958 | 4/2003 |

OTHER PUBLICATIONS

Gagnadre I et al: "Circular patch antenna sensor for moisture content measurement on dielectric material" Electronics Letters, IEE Stevenage, GB, pp. 1167-1168, XP006003058 ISSN: 0013-5194 the whole document.

Ebbe Nyfors and Perth Vainikainen: Industrial Microwave Sensors, 1989, XP002334964 Gleichungen 3.49, 3.47, 3.45, 3.44, 3.25, 3.21 p. 145, paragraph 1.

Knoechel R: "Technology and Signal Processing of Dielectrometric Microwave Sensors for Industrial Applications" Transactions of the Metal Finishers Association of India, XX, IN, Bd. 7, Jan. 1, 2000, Seiten 65-105, XP002327685.

Krause H-J et al; "Dielectric microwave resonator for non-destructive evaluation of moisture and salinity" Sep. 29, 2006, 9th European Conference on NDT: ECNDT Berlin 2006; Sep. 25-29, 2006, European Federation for Non-Destructive Testing, Berlin, pp. 1-12, XP008104806 ISBN: 9783931381868.

Apr. 26, XP002570607 Gefunden im Internet: URL:http://web/archive/org/web/20061006111343/222.ecndt2006.infor/doc/ECNDTFinalProgramme.pdf> [gefunden am Feb. 26, 2010].

H-J, Krause, N. Klein, F. Dumat, E. Rath, P. Haardt, W. Leschnik: "Zerstoerungsfreie Pruefung des Feucht- und Salzgehaltes von Vaustoffen mit einem dielektrischen Mikrowellen-Resonator hoher Guete" DGZFB-Berichtsband 91: Feuchtetag 2004 MIT Workshop Onsiteformasonry; Nov. 18-19, 2004 sEITEN 175-185, XP009130057 Berlin.

Herrmann R et al: "Feuchtemessung MIT Mikrowellen-Resonatoren" Technisches Messen TM, R. Oldenbourg Verlag. Muchen, DE, Bd. 64, Nr. 11, Nov. 1, 1997, Seiten 447-452, XP000738914 ISSN: 0171-8096.

King R J: "On-lin Industrial Applications of Mircrowave Moisture Sensors" Sensors Update, Wiley-VCH, Weinheim, DE, Bd. 7, Jan. 1, 2000, Seiten 109-170, XP002400304.

Goeller A: "Midrowellen-Feuchtemessung—Auswahl Geeigneter Applikatoren" Technisches Messen TM, R. Oldenbourg Verlag. Muchen, DE, Bd. 64, Nr. 11, Nov. 1, 1997, Seiten 426-432, XP000738912 ISSN: 0171-8096.

* cited by examiner

METHOD FOR IDENTIFYING A SAMPLE IN A CONTAINER, E.G. WHEN CONDUCTING A TRAVELER SURVEY IN THE CHECK-IN AREA, BY DETERMINING THE RESONANCE FREQUENCY AND THE QUALITY OF A DIELECTRIC RESONATOR TO WHICH THE CONTAINER IS ARRANGED

BACKGROUND OF THE INVENTION

The invention relates to a method for identifying a sample in a container and to an associated measuring device.

A method and an apparatus for measuring the complex dielectric constant of a material by evaluating the degree of detuning of an RF resonator, which is introduced by the presence of the material, is known From DE 43 42 505 C1, in which an RF transmitter for transmitting high-frequency electromagnetic fields of selectable frequency into the RF resonator, a receiver for the resonator field, and a measuring circuit connected to the receiver are provided, whereby the amplitude of the received radio-frequency signals can be determined by way of the measuring circuit.

A variety of methods are known for determining the dielectric properties of materials, which typically are indicated as the dielectric constant Fr and the loss angle tan ($\delta$), or as the complex dielectric constant $\in=\in'-i\in''$. Such methods are used, for example, for determining the moisture of materials. These methods are based on the high dielectric constant and the large loss factor of the water in the material and are highly important in industry, for example in measuring the moisture in chemicals, foods, tobacco, coffee, and the like.

In the resonance methods for determining moisture by way of microwaves, the material to be analyzed is introduced into a cavity resonator and the detuning of the cavity resonator caused by the presence of the material is measured, the resonance curve being followed and measured by varying the irradiation frequency. The shift in the resonance frequency and the increase in the resonance half-width value, or the change in quality of the resonator, can be used to derive the dielectric constant, and hence the water content of the material, if the material composition and density are known. For this purpose, calibration curves are generally required, which are obtained by prior measurement of respective substances having different known moisture levels. In most known methods, a separate measurement of the material density is also required.

A method for determining the material moisture content with the aid of a cavity resonator is known from DE 40 04 119 A1 in which, for a known material, by way of a defined selection of the field course of the cavity resonator in the region of the sample to be analyzed, the material moisture content and material density can be determined independently of each other, using a calibration curve wherein the resonance frequency determined by following the resonance curve and the half-width value of the resonance line are determined and evaluated. Again, it is necessary to introduce the material to be analyzed into the cavity resonator in the form of a sample.

From the article "Ein Dielektrizitätskonstanten-Messplatz zur Untersuchung optischer Kristalle im Mikrowellenbereich (A dielectric constant measuring station for the analysis of optical crystals in the microwave range)" in: Kristall und Technik, Volume 10, No. 6, 1975, pp. 695-700, by E. Wehrsdorfer et al., a method similar to that described above is known, wherein the dielectric constant of a sample is determined by loading a cavity resonator operated in the microwave range with a sample. The change in resonance frequency and quality caused by the presence of the sample in the cavity resonator is determined by measuring the resonance curve after introducing the sample into the cavity resonator.

The printed East German patent specification 1 38 468 discloses a method for measuring the complex dielectric constant of dielectric plates which are metallized on one side. For the measurement, a dielectric resonator is placed on the non-metallized side of the plate, and the resonator $TE_{011}$ mode is excited. The metallized side of the plate acts as the end point of the resonance-capable system. The change in resonance frequency compared to the case in which the dielectric resonator is placed on a metal plate can then be used to determine the dielectric constant of the plate material if the thickness is known.

Recently, commercially available moisture sensors allow the sensor to scan the sample within milliseconds. In this process, the product moisture can be continuously detected as a function of the density and weight, with changes in the product temperature being compensated for automatically. These methods are used, for example, in the manufacture of products in the ceramics industry.

The disadvantage of the known methods, which are based on HF technology, is that they are limited to determining the complex dielectric constant of a sample having known dimensions. This means that the geometry and the exact dimensions of the sample must be known in order to determine the real and imaginary parts of the complex dielectric constant based on a measured quality and frequency shift.

It is also disadvantageous that, in order to determine the dielectric constant, a sensor must be brought in contact with the sample, which should be avoided, particularly with hazardous samples, such as acetone or other flammable fluids.

SUMMARY OF THE INVENTION

It is the object of the invention to provide a method and a device, which allow a sample in a container to be identified without necessarily having to open the container.

The object is achieved by a method and a device. Advantageous embodiments are apparent from the following discussions and referenced drawings.

The method for identifying a sample in a container according to the invention provides for performance of the following steps:

the container with the sample is disposed relative to a resonator such that the resonant electric field of the resonator can penetrate at least part of the sample in the container, a high-frequency signal is coupled into the resonator in order to excite a resonant mode of the resonator, the resonance curve of at least one resonant mode is measured with and without the sample container, the sample is identified based on the determined change in the resonance frequency.

With the method according to the invention, the sample is identified in a simple and very rapid manner, without having to open the container for the sample. As a result, in a particularly advantageous manner, when the samples are unknown, the risk of exposing humans and objects to danger caused by hazardous samples, such as acids or acetone, is minimized. The method is a contactless method and in this sense is particularly advantageous, since no contact with the sample is required for identification.

The sample is identified based on the determined change in the resonance frequency as compared to a measurement without the sample container, which is to say, as compared to air.

In a particularly advantageous embodiment, the method according to the invention is very reliable in differentiating ingestible from non-ingestible fluids and solid matters. This makes the method particularly useful for check-in areas when processing travelers.

The behavior of non-metallic materials with respect to alternating electromagnetic fields is generally described by a complex dielectric constant $\epsilon_r = \epsilon_1 - i\epsilon_2$. Both the real and the imaginary parts are generally frequency and temperature-dependent. If a substance having a given $\epsilon_r$ is introduced into the alternating electric field of a resonator, the real part ($\epsilon_1$) results in a shift of the resonance frequency, and the imaginary part ($\epsilon_1$) results in a decrease in quality.

The absorption behavior, in particular of fluids in the microwave range, is described by the relaxation of the molecules upon deflection from the state of equilibrium by the alternating electric field of the injected electromagnetic wave. Algebraically, the behavior can be described by a complex dielectric constant $\epsilon(f)$ that is dependent on the frequency f of the alternating field.

$$\varepsilon(f) = \varepsilon_1(f) + i \cdot \varepsilon_2(f) = \frac{\varepsilon_s - \varepsilon_\infty}{1 + i2\pi f \tau} \quad (1)$$

wherein $\epsilon_S$=static dielectric constant; $\epsilon_\infty$=optical dielectric constant; $\tau$=relaxation time; f=excitation frequency.

According to the equation above, different fluids differ markedly by the values of the static dielectric constant $\epsilon_S$ and the relaxation time $\tau$. Above a frequency of $f=1/2\pi\tau$, the real part of $\epsilon$ decreases drastically and the imaginary part has a maximum.

With the method described, it is now possible to identify fluids in arbitrary, non-metallic containers by way of the properties of the fluids, based on different values for $\epsilon_S$, $\epsilon_\infty$, and $\tau$ within a time period of approximately 100 milliseconds, without having to open the container. To this end, the diameter of the container should not be much smaller than the resonator diameter, so that, optionally, a plurality of resonators having different diameters must be used to cover all possible bottle sizes.

In performing the method, liquid samples are, in particular, selected and identified, but solid samples are not excluded. It is also conceivable to analyze gaseous samples.

To this end, the sample container is disposed outside the resonator in a mounting that is preferably at a known distance from the resonator.

For a given geometry and type of resonator material, the frequency for exciting a resonant mode of the resonator is known. Therefore, advantageously a signal having this frequency can be coupled into the resonator in a simple manner so as to excite a resonant mode of the same.

Microwaves are preferably selected in a range of 1 GHz to 30 GHz, for exciting a resonant mode. In this range, it is advantageous that different fluid samples exhibit significantly different values in terms of their complex dielectric constants. Furthermore, in this frequency range compact dielectric resonators having high quality can be implemented. The resonant electric field of a mode of the resonator penetrates at least part of the sample in the container when performing the method according to the invention.

The values of the resonance frequency, and optionally of the quality, are determined during the method, with and without the sample container, based on the measured resonance curve.

It was then found, as part of the invention, that analyzing only the change in quality of the resonator resulting from the sample in the container as a function of the distance from the sample to the resonator appears to be insufficient for definitive identification of the sample, and in particular of a fluid, even if the distance from the sample container to the resonator is varied and measured again.

It was furthermore found that, according to the inventive identification of the sample, having knowledge of the change in resonance frequency is sufficient in order to identify the sample.

When measuring only the resonance frequency, consideration must be given to the fact that knowledge of the distance from the sample to the resonator is preferably required for the identification of the sample. This means that, for differently shaped containers that are placed in the mounting, the distance must be determined metrologically and set to a predetermined value. Measuring only the resonance frequency is thus sufficient for standardized sample containers. In the case of differently shaped sample containers, however, different thicknesses of the container walls may result in misinterpretation.

In an advantageous embodiment of the invention, the quality, and particularly advantageously the reciprocal quality, are also determined during the method and are related to the resonance frequency and represented. Thus, in a particularly advantageous manner, the definitiveness and selectivity during identification of the sample is increased, and specifically by means of a single measurement of the resonance curve with the sample container and without the sample container (compared to air) such that the distance from the sample container to the resonator is irrelevant. In a particularly advantageous embodiment, an extremely simple and reliable differentiation between hazardous and non-hazardous samples is furthermore possible, even for untrained staff, as a result of the manner in which the result is represented.

Therefore, for definitive and selective identification, both parameters, namely the change in the resonance frequency and in the quality, should be related to each other. In this case then, a single measurement with and without the sample is sufficient for identifying the sample, even without precise knowledge of the distance from the sample container to the resonator.

The determination of the reciprocal quality and resonance frequency changed by the sample and the representation of the relation between reciprocal quality and resonance frequency are particularly suited for very rapid identification of the sample, regardless of the type of sample container.

In particular, this relationship advantageously allows non-ingestible fluids to be differentiated from ingestible fluids, or generally speaking, hazardous samples from non-hazardous samples.

Due to the linear relation between the resonance frequency and reciprocal quality during the measurement of the two variables, in a particularly advantageous embodiment it is possible to identify the sample independently from the distance between the sample and the resonator. As a result, fluids can be identified for all shapes of containers without having precise knowledge of the distance. This means that a mounting for the sample container having a fixed distance from the resonator can be selected for identifying fluids or the sample in arbitrarily shaped containers.

Consequently it can be stated, within the framework of a perturbative analysis, that the relation between the change in the resonance frequency and the change in the reciprocal quality of the resonator is largely independent from the container geometry, and also from the distance from the container to the resonator.

In particular, the resulting relationship between the reciprocal quality and the change in the resonance frequency is therefore suited for identifying the sample.

The conclusion of this analysis is:

$$\frac{\Delta(1/Q)}{\Delta f / fr} = const. \quad (2)$$

This means that the reciprocal quality levels measured at different distances are largely linearly dependent on the resonance frequency, and the gradients of the resulting straight lines are characteristic of the substance.

As a result, in a highly advantageous manner, the contents of small and large, rough and smooth, angular and bulged containers, bottles, cans, canisters and the like, however they may be configured, can be inspected, without having to open them and without having to measure them at different distances from the resonator.

Without any further limitation, a sample container or objects made of glass or plastic, as well as ceramic, with or without partial metallization, and with or without labels, can be analyzed, as long as the wall of the sample container in the direct vicinity of the resonator is not metallized, and the resonant electric field of the resonator can at least partially penetrate the sample in the container.

In one embodiment of the invention, the resonance curves are measured multiple times in order to identify the sample, and in each case the resonance frequency, and optionally the quality of the resonator, are determined from the resonance curves and are related to one another.

In a further embodiment of the invention, these measurements can be performed at different distances from the sample to the resonator. To this end, the position of the resonator, or of the resonators, is preferably shifted so as to change the distance to the sample.

It is also possible, however, to consecutively excite different resonant modes of the same resonator, thereby performing the identification of the sample with increased selectivity. Through measurements at different frequencies, the method advantageously becomes even more definitive and selective, due to the strong frequency dependencies of the complex dielectric constant of many fluids.

Advantageously, the resonance curves of the resonator associated with the respective mode are measured by exciting different resonant modes.

In a particularly advantageous embodiment, a method is performed in which the resonant modes of more than one resonator are excited. In this way, for example, different resonant modes of resonators having identical designs can be excited during the method. However, it is likewise possible for the same resonant modes of resonators not having identical designs to be excited.

In the case of multiple measurements, the free combination of the parameters consisting of
  a different distance from the sample to the resonator,
  a suitable selection of one or more resonators,
  consecutively performed excitations of different resonant modes of a resonator,
  and/or of an arrangement of a plurality of resonators having identical designs, the different resonant modes of which are excited,
  and/or of an arrangement of multiple resonators not having identical designs, the identical resonant modes of which are excited,
provides for many possible variations in which the method can be performed.

Multiple measurements during the method, in particular after changing the distance from the sample container to the resonator, likewise result in precise identification of the sample, and thus in impeccable classification of the sample into ingestible or non-ingestible or, generally speaking, hazardous or non-hazardous samples, or fluids.

The device according to the invention for performing a method comprises at least one resonator and a mounting for a sample container, and further a first means for exciting a resonant mode of the at least one resonator, wherein the resonator and the mounting can be disposed relative to one another such that, after exciting a resonant mode of the resonator, the resonant electric field of the resonator is able to penetrate a sample in a sample container at least partially, and further comprising a second means for measuring the resonance curve of the resonator. The device is characterized in that it comprises a third means for determining the resonance frequency.

As a matter of course, the sample, or the sample container, is not part of the device according to the invention.

The resonance frequency is preferably also represented by the third means as a function of the distance from a sample container to the resonator, for example on a monitor.

The distance between the sample container and the resonator can be selected as part of the method so that quality levels between 100 and 1000 are obtained. Quality levels in this range of values are easy to measure, and the selectivity for the differentiation of fluids is, in particular, very good. In this connection, the distance may range between 0 and 5 millimeters. The mounting for the sample container in the device must be designed accordingly and disposed relative to the resonator.

In a further embodiment of the invention, the device is preferably configured so that the distance between the mounting for the sample container and the resonator can be varied in millimeter intervals.

Multiple measurements at different distances from the sample container to the resonator particularly advantageously ensure that the sample can be identified without having to compute further parameters, such as the change in quality. The resonance frequency curves thus obtained, as a function of the distance from the sample to the resonator, allow the sample to be identified by way of the gradient of the curve.

In one embodiment of the invention, the device comprises a microwave oscillator, in particular a variable-frequency microwave oscillator, or a broadband amplifier having a resonator in a feedback circuit, as the first means for exciting a resonant mode of the resonator.

In a further embodiment of the invention, the device comprises a detector diode, or a bolometric power detector, or a heterodyne receiver, as the second means for measuring the resonance curve of one or more oscillation modes, from which the respective resonance frequencies, and optionally the quality levels, are determined.

In a further particularly advantageous embodiment of the invention, the device comprises a network analyzer, and in particular a vectorial network analyzer. Network analyzers as defined in the invention comprise both variable-frequency microwave oscillators and heterodyne receivers as first and second means for the device.

As the third means, the device may comprise a computer having suitable software. The software determines the resonance frequency from the resonance curve.

Advantageously, the software is part of a computer, or of a network analyzer, and advantageously outputs, on a monitor, the resonance frequency as a function of the distance between the sample container and resonator.

In a particularly advantageous embodiment, the third means also determines the quality of the resonator with and without the sample. For that purpose, the resonance frequency corresponds to the frequency at which a maximum of the resonant amplitude takes place. The quality is derived from the relation between the resonance frequency and the half-width value of the resonance curve.

In a further, particularly advantageous embodiment of the invention, the third means of the device also represents the determined resonance frequency as a function of the measured reciprocal quality, thus allowing a quick identification of the sample to be performed with high selectivity.

As the third means, software performs these steps automatically and consecutively.

In a particularly advantageous embodiment, the software can be configured so that, in identifying a sample, the quality value, and in particular the reciprocal quality value, and the resonance frequency with and without the sample container are computed from the measured resonance curve. Subsequently, the software determines the relationship between the change in the resonance frequency and the change in the reciprocal quality, with respect to the value without the sample container. This number indicates the gradient of the straight line.

In the simplest instance, the software determines whether a sample is ingestible or non-ingestible exclusively by way of the gradient of the determined straight line.

Advantageously, the software can then output the result, preferably by way of a message on the monitor.

The software is preferably configured so as to enable a suitable graphical representation and classification of the sample into ingestible or non-ingestible samples on an output device, such as a monitor or printer. To this end, starting from zero without the sample, the software preferably displays a range of gradients characteristic of ingestible fluids or solids. As soon as a fluid, or a solid, outside this range is identified, it is represented in a suitable manner, for example visually.

It is conceivable that the resonator is disposed inside the device in a metal housing having at least one opening. The opening of the housing for the resonator is oriented toward the sample container. The opening of the housing is permeable by the electromagnetic fields of the resonator.

In particular, dielectric resonators made of low-loss microwave ceramics having a relatively high dielectric constant $\in_r$ have high quality levels, even with partially open geometries. The $TE_{01\delta}$ resonance, characterized by an azimuthally peripheral E-field and an axial dipolar H-field, is generally very stable for a cylindrical ceramic with a high dielectric constant. The same also applies to higher $TE_0$ resonances, the field distributions of which are, in terms of rotation-symmetry, rotation symmetrical. The opening in the metal housing ensures that the electric fields of the resonator can partially penetrate the sample.

It is also conceivable, within the scope of the invention, to employ the so-called "whispering gallery resonances", which are hybrid resonances having a high azimuthal mode index n (typically greater than n=8), which have very low radiation losses, it being possible to operate some of these even without any housing at all.

The distance from the mounting for the sample container to the resonator can be a few millimeters to centimeters, depending on the dimensions, the geometry of the sample container, and the selected mode of the resonator.

For the purpose of precise alignment of the sample container, the mounting for the sample container has at least two V-grooves. It is then possible, for example, to align containers such as bottles, cans, or canisters, precisely horizontally with respect to the longitudinal axis thereof, whereby the axis of a resonator intersects the axis of the container at a right angle.

The device according to the invention is not, however, limited to this embodiment.

In a particularly advantageous device, a sample container is placed on a sloped mounting surface, and the position of the container on this sloped surface is fixed by a mounting support surface, which is disposed perpendicular thereto. In this case, in a particularly advantageous embodiment, two resonators can be disposed, one with the screen parallel to the sloped surface of the mounting and the second perpendicular thereto under the bottom of the sample container, so that the identification of the sample is performed both through the lateral walls of the sample container and through the bottom of the sample container.

Thus, particularly advantageously, the resonator that is provided under the sloped surface captures the maximum possible volume of the sample when the sample container is filled only partially with sample material, thereby contributing to increasing the accuracy and reproducibility of the measurement. In addition, the resonator disposed under the bottom of the sample container is particularly advantageously used for identifying the sample in containers having small diameters.

The angle of the sloped mounting surface with respect to the horizontal line, and hence the angle that the sample container encloses to the horizontal line, should preferably range between 20 and 50 degrees.

Advantageously, the device has a cylindrical dielectric resonator. The particularly advantageous effect is that many modes have high quality levels, due to the high symmetry. As differs from spheres and hemispheres, which likewise exhibit high quality levels, cylindrical dielectric resonators are easy to produce, and are commercially available.

In a further embodiment of the invention, the device may be characterized in that the resonator is disposed central-symmetrically in the metal housing.

The metal housing may have a cylindrical shape.

The opening in the housing of the resonator may be implemented by a central, circular cylindrical screen.

The sample container and the housing for the resonator are advantageously positioned relative to one another so that the lowest point of the container is disposed above the center of the opening of the housing or the resonator. As a result of the high symmetry of this arrangement, potential resonator radiation losses are minimized, and possible deviations from the linear relation between the reciprocal quality and the resonance frequency are minimized.

The device advantageously comprises a variable-frequency microwave oscillator for coupling microwaves into the resonator and for exciting the resonant mode. Thus, in a manner that is advantageous in turn, multiple measurements of the resonance frequency and the quality are possible.

In a particularly advantageous embodiment of the invention, the device comprises a network analyzer for generating the microwaves and for recording the resonance curve, which is used to determine the resonance frequency and quality.

In a further embodiment of the invention, the device may comprise multiple resonators, and hence form a measuring station comprising multiple resonators having, or not having, identical designs.

Resonators not having identical designs as defined in the invention are, for example, resonators having different diameters.

The device advantageously comprises multiple resonators, which are disposed relative to one another such that they represent the shape of the sample container. If, for example, the method is to be performed for identifying the content of part of a shoe as the sample, it is possible, for example, to dispose two resonators for the heel, one resonator for the toe-cap, and for example two more resonators for the remainder of the sole in the measuring station. To this end, a person wearing this shoe would no longer have to take it off for examination. Advantageously, in this way X-ray examinations of shoes that are taken off, for example in the check-in area for processing travelers, can be replaced by the method according to the invention, providing qualitative information.

The invention will be described in more detail below with reference to embodiments and the attached figures.

BRIEF DESCRIPTION OF THE DRAWINGS

Shown in the attached are the following.

Figure 1:
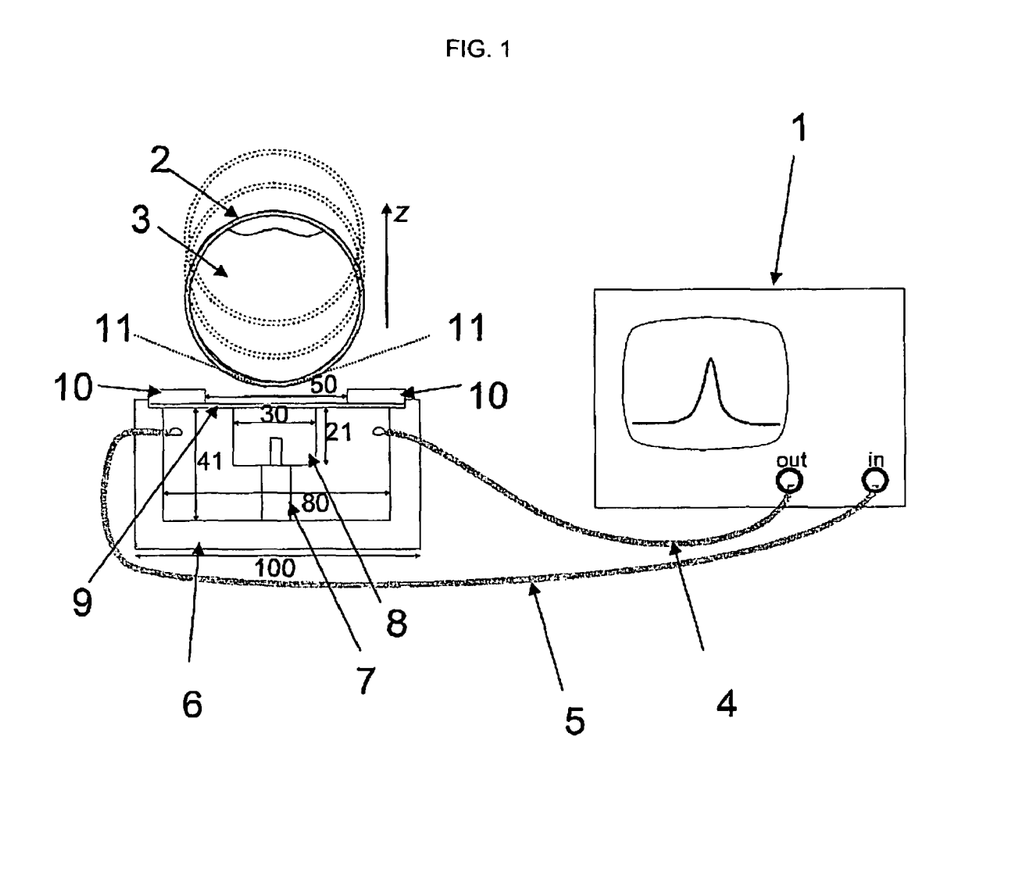
FIG. 1: An embodiment of the device according to the invention.

The device according to the invention, according to a first embodiment of the invention, comprises a dielectric resonator 8, which is disposed inside a metal housing 6 made of aluminum, which is open at least from one side (FIG. 1).

DETAILED DESCRIPTION

The dielectric resonator 8 comprises the microwave ceramic, barium zirconate titanate (BZT), wherein $\in_r$=28. A cylindrical dielectric microwave resonator was made from this, and this was disposed in a partially-open metal housing 6. The cylindrical special ceramic for microwaves (radius a=15 mm, height H=21 mm, bore 4 mm) is disposed on a Teflon holder 7, which is screwed into a partially-open aluminum cylinder (external diameter 100 mm, internal diameter 80 mm, height 54 mm). The resonator is covered with a cover 9 comprising a 1 mm thick Teflon film. This effectively fixes the resonator 8 in the housing 6 and protects the resonator 8 from soiling. The partially-open cylindrical aluminum housing 6 of the resonator 8 was further covered with an aluminum cover screen 10 having an outside diameter of 90 mm, and an inside diameter of 50 mm, so as to increase the quality of the resonator. Coaxial coupling and decoupling lines 4, 5, each having a coupling loop measuring approximately 3 mm, are disposed surface normal in the axial direction on both sides of the resonator ceramic. A coaxial coupling line having a coupling loop measuring approximately 3 mm (surface normal in the z-direction) is located on the left, and a loop for decoupling having the same dimensions and orientation is provided on the right. The approximate resonance frequency of the $TE_{01\delta}$ mode of the ceramic cylinder can be determined with the formula $$f_0 [\text{GHz}] = \frac{34}{a[\text{mm}]\sqrt{\varepsilon_r}} \left( \frac{a}{H} + 3.45 \right) \tag{3}$$

Using the geometric parameters described above, $f_0$=1.78 GHz is determined as the excitation frequency of the resonator 8.

A bottle 2 having a fluid 3 as the sample is measured at a variable distance z (dotted circles) from the cover screen 10.

The resonator 8 was connected, by the two coaxial coupling lines 4, 5, to the reflection and transmission port of a vectorial network analyzer 1 (Hewlett Packard 8752A). The frequency-dependent transmission was measured with an HF output power of 0 dBm. In order to perform the measurement, the fluid-filled bottle was positioned at different distances z from the resonator. In order to perform a well-defined and known distance-dependent measurement, a two-arm mounting having two V-shaped grooves 11 was manufactured from PVC, one of which is shown in FIG. 1 outside the image plane. Thus, bottles 2 having different shapes and surface finishes can be placed into the two V-shaped grooves 11. The bottle 2 was adjusted by means of a stand so that the bottle wall rested on the metal cover screen 10 of the resonator 8. The lowest point of the bottle 2 may possibly be located above the center of the dielectric resonator 8.

The arrangement can, of course, also be tilted by ninety degrees, taking care that the fluid reaches the wall of the bottle in the region of the smallest distance between the resonator and bottle edge, so that the electric field penetrates the fluid.

The bottle 2 was positioned symmetrically with respect to the resonator 8 such that the resonator axis intersects the bottle axis at a right angle. The bottle 2 was then moved vertically away from the resonator 8 in 1 mm increments by means of a micrometer screw. At each position, a determination of the resonance frequency and the quality was performed.

Accordingly, the quality and resonance frequency for the excited modes are measured so as to identify the bottle content. By collecting multiple measurement values for different distances from the bottle 2 to the resonator 8, different fluids are identified even more definitively.

Figure 2:
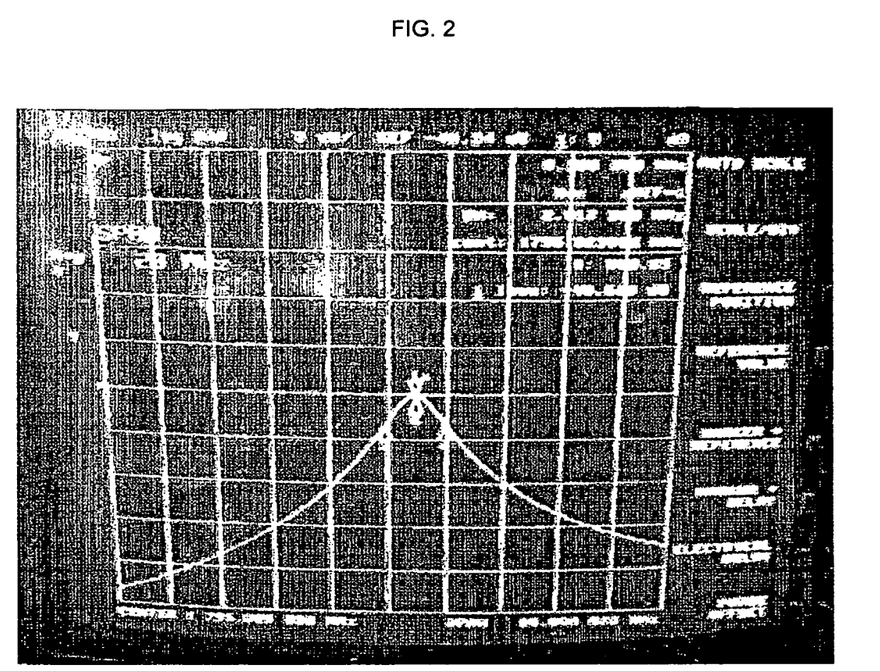
FIG. 2: A transmission spectrum for a dielectric resonator with a fluid-filled bottle placed on it.

FIG. 2 shows a typical reflection spectrum measured for a fluid-filled bottle. The sweep bandwidth of the HP 8752A was selected at 10 MHz, 20 MHz, or 50 MHz, depending on the width of the resonance.

Figure 3:
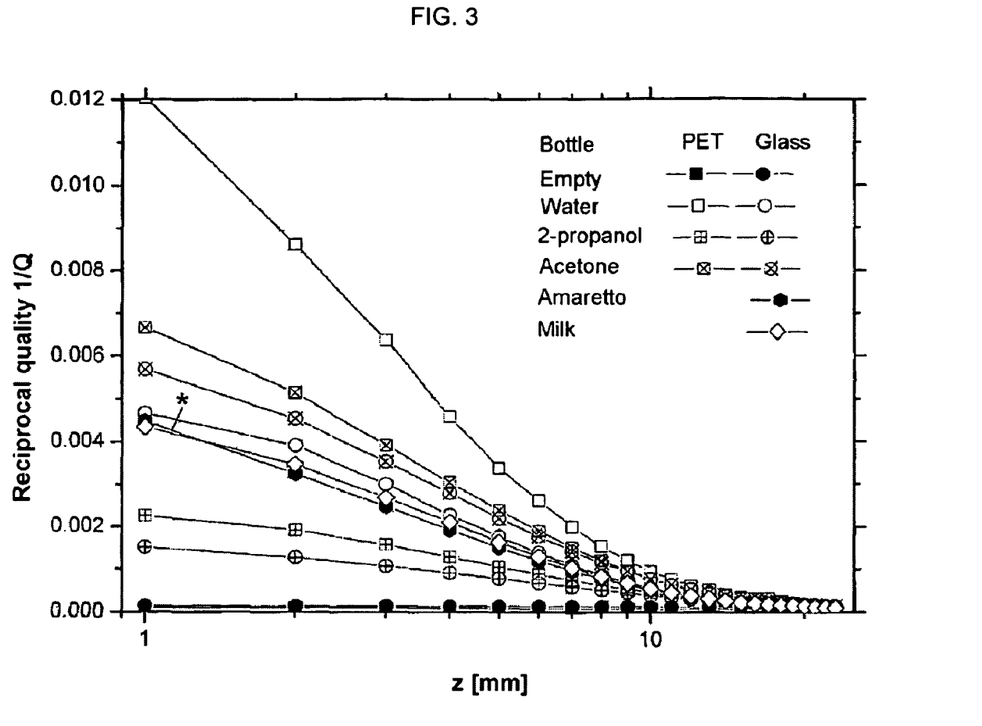
FIG. 3: The quality determined from the measured resonance curve as a function of the distance z from the bottle to the cover screen, for different fluids, and for different bottle types.
Figure 4:
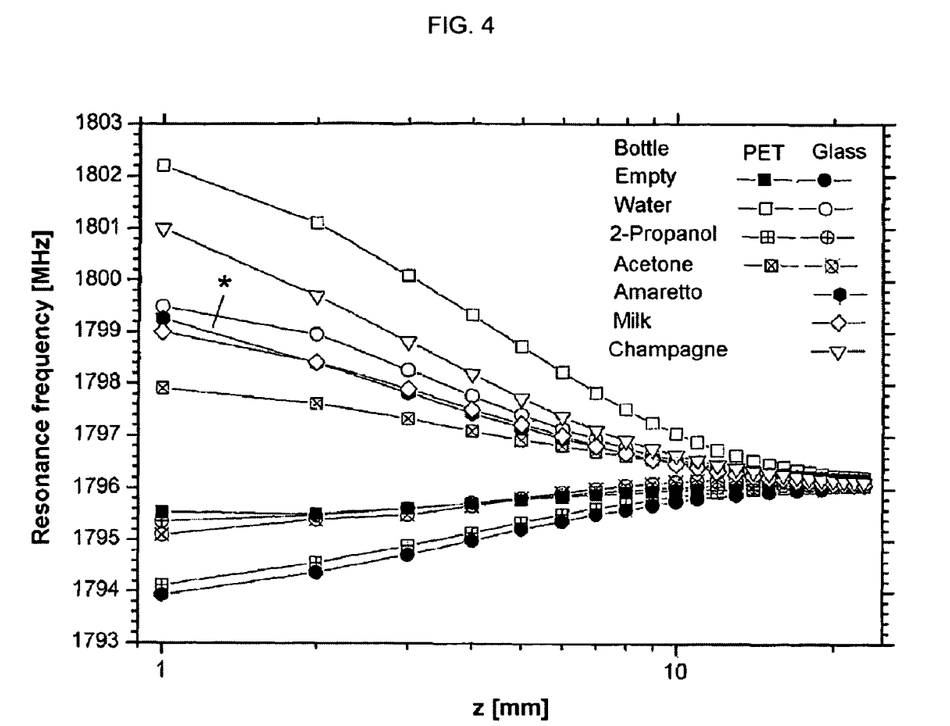
FIG. 4: The resonance frequency determined from the measured resonance curve as a function of the distance z from the bottle to the cover screen, for different fluids, and for different bottle types.

FIG. 3 and FIG. 4 each show the respectively collected measurement values in relation to the reciprocal quality that was determined, and the resonance frequency that was determined, as a function of the distance from the bottle 2 to the resonator 8. The distance z is shown in logarithmic representation.

A commercially available 1-liter bottle of the Coca Cola® brand was selected as the PET bottle for all the results illustrated.

Unless stated otherwise, a commercially available 0.7-liter water bottle having a studded surface was used as the glass bottle.

In FIGS. 3 and 4, solid circles and squares represent, in each case, air-filled bottles made of polyethylene (PET bottle: square) and glass (circle) as a function of the distance from the bottle to the resonator. The actual reference is, in turn, a measurement compared to air, which is to say without the sample container. The same also applies to the results in FIG. 5 (see below).

In addition to tap water (empty square: PET bottle; empty circle: glass bottle), the quality and the resonance frequency of 2-propanol (vertical cross in square: PET bottle; vertical cross in circle: glass bottle), acetone (diagonal cross in square: PET bottle; diagonal cross in circle: glass bottle), almond liqueur (solid black octagonal circles, lines in FIG. 3 and FIG. 4 marked with "*" to allow differentiation, commercially available rectangular glass bottle of the brand Venezia® having high surface roughness), milk containing 3.5% fat (empty diamond), and for the measurement of the resonance frequency, sparkling wine (downwardly pointed empty triangle) were measured. The measurements with sparkling wine and milk were in turn performed in commercially available 0.7-liter water bottles, as shown above.

Both variables, which is to say the resonance frequency and quality, continuously decrease as the distance between the bottle and resonator increases.

The ingestible beverages (water, liqueur, milk, and sparkling wine) each have higher resonance frequencies than the non-ingestible chemicals, 2-propanol and acetone (FIG. 4).

A similar statement, however, is not possible for the quality (FIG. 3) of the resonance. Here, the reciprocal quality as a function of the distance of the sample container (lower edge of the bottle) from the resonator is shown. In this case, an apparently indiscriminate sequence of ingestible and non-ingestible fluids is shown.

Figure 5:
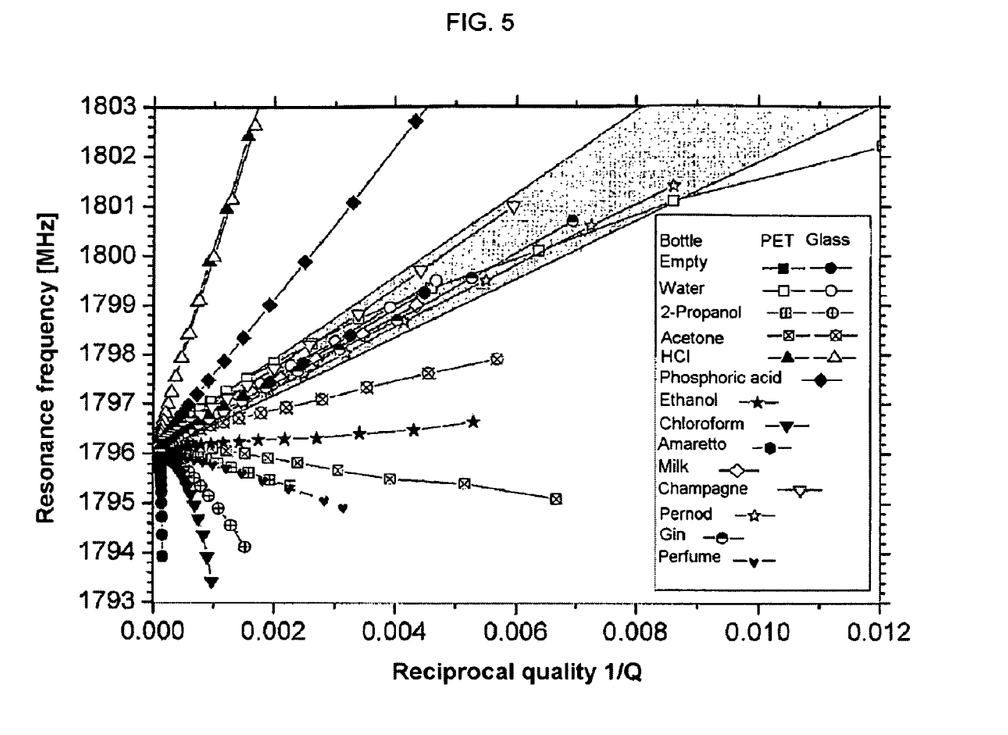
FIG. 5: The relationship, according to the invention, between the measured resonance frequency as a function of the reciprocal quality for different distances z, different fluids, and different bottle types and shapes. The measurement points for the empty PET bottle are hidden behind the measurement points for the empty glass bottle.

FIG. 5 shows a particularly advantageous method with an exhaustive representation of the resonance frequency as a function of the reciprocal quality 1/Q at different distances from the sample container to the resonator. FIG. 5 clearly shows that the reciprocal quality coefficient is largely proportional to the measured change in the resonance frequency according to sample, and that consequently measurement at different distance values produces a largely linear relation between the resonance frequency and reciprocal quality. In practice, this means a very fast and precise identification of the fluid.

The distance between the sample container and resonator should preferably range between 0 and 5 millimeters. For the lines shown in FIG. 5, this corresponds to the six values with the highest reciprocal quality values and resonance frequencies. This results in quality levels between approximately 100 and 1000 for most fluids (FIG. 5). Quality levels in this range of values are easy to measure, and the selectivity for the differentiation of different fluids is very good.

The region highlighted in gray constitutes the range of ingestible fluids. In addition to the fluids shown in FIGS. 3 and 4, in FIG. 5 the alcoholic beverages Pernod and gin, as well as a popular perfume are also shown. Furthermore, as further chemicals, ethanol and chloroform as well as the acids hydrochloric acid and phosphoric acid were measured.

The results allow the following conclusions:
1. The range of ingestible fluids is narrow. As a result, an unknown fluid can be quickly and reliably categorized as ingestible or non-ingestible, or hazardous and non-hazardous.
2. The range of ingestible fluids exhibits straight lines with a positive gradient.
3. The gradients of the curves for the ingestible fluids are largely independent of the material (glass, plastic) and are not influenced by the exact shape of the bottles, or by paper or plastic labels.
4. Flammable fluids exhibit clearly digressive gradients, allowing for clear differentiation.
5. Outside the range of ingestible fluids, acids also exhibit positive gradients. The straight lines determined exhibit a higher gradient than the ingestible fluids.
6. Outside the range of ingestible fluids, acetone in glass and ethanol in plastic also exhibit positive gradients. The straight lines determined for these exhibit a smaller gradient than that of the ingestible fluids.
7. Negative gradients occur for all non-ingestible fluids and for empty bottles made of PET and glass.

As a general result of the invention it can thus be established that there are clear physical parameters and representations of the same, which allow a fast and reliable identification of a sample in a closed container.

The dependencies in the curves depending on the bottle material, observed for flammable fluids, and the occurrence of negative gradients, can be explained qualitatively as follows. For water, the increase in the resonance frequency observed as the distance to the bottle decreases is due to the fact that electric field energy is increasingly redistributed into a medium having a high dielectric constant, resulting in an increase in the electric field energy (positive gradient). The magnetic field energy apparently plays only a small role in this. For fluids having a lower dielectric constant, the influence of the effective reduction of the electric field volume by a partial reflection on the bottle prevails, resulting in an increase in the resonance frequency (negative gradient). This is also the reason why a negative gradient is observed for an empty bottle. Depending on which influence prevails, the algebraic sign of the gradient may also be determined by the bottle material, as was observed for acetone.

Due to the high frequency dependency of $\in$ for fluids in the microwave frequency range, it is to be expected that a different chart will be obtained for other frequencies. For example, it is to be expected that an excitation frequency in the range of 5-10 GHz results in clear differentiation of alcoholic beverages according to the alcohol content of the same.

Due to the fact that the curves shown in FIG. 5 are straight lines, which intersect at one point (namely, the f and 1/Q value of the resonator without bottle), every fluid can be fully characterized by measuring it at only one distance value. Such a measurement can be performed within a time period of approximately 100 milliseconds. Due to this fact, the method is suited for identifying the content of non-metallic bottles during check-in at airports.

Figure 6:
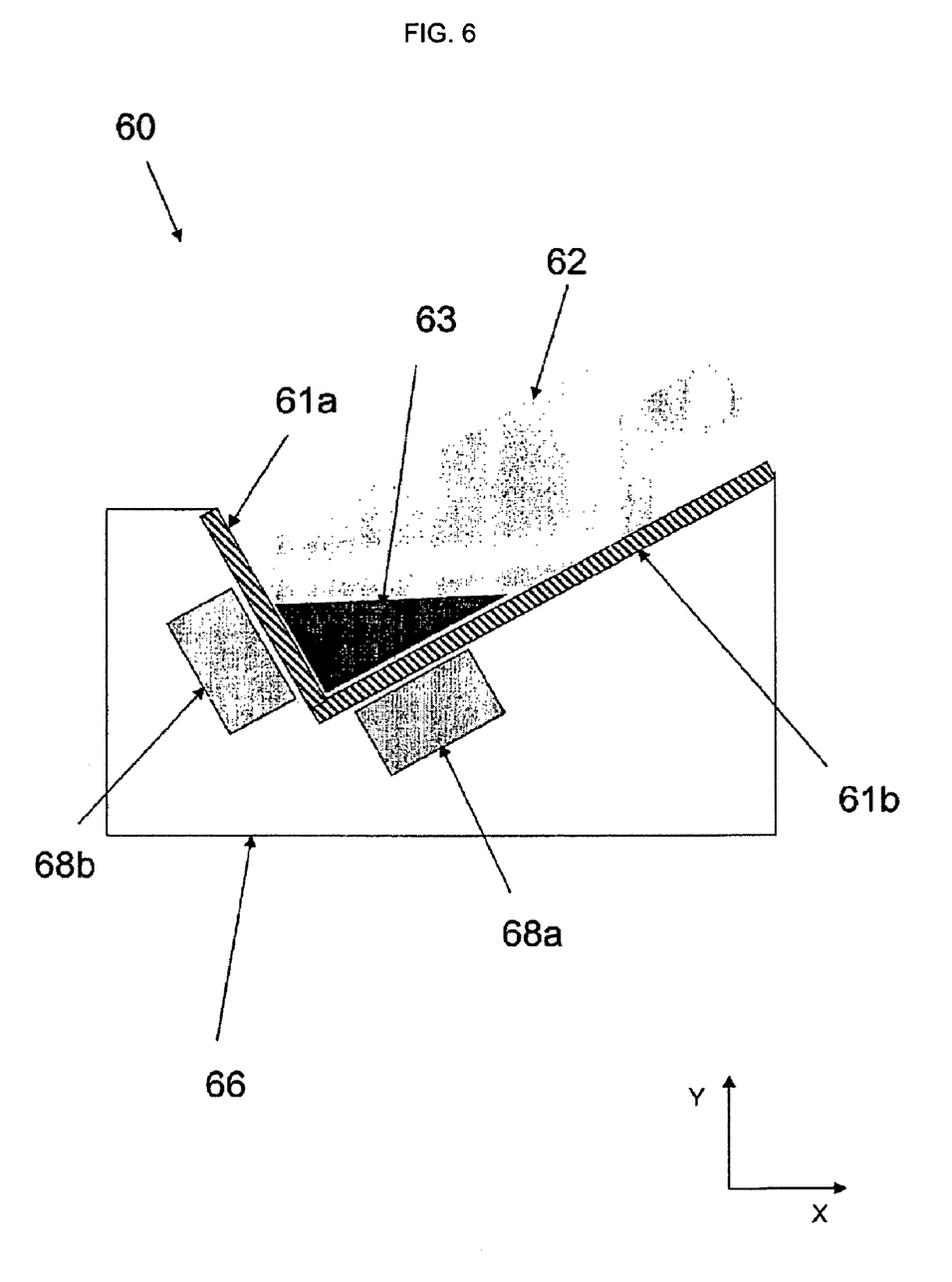
FIG. 6: A further embodiment of a device according to the invention.

FIG. 6 is a schematic illustration of a further advantageous embodiment of the device according to the invention.

In the illustration, the mounting 61a, 61b is disposed in the device 60 according to the invention so that a sample container disposed on the sloped part 61b of the mounting, in this case a bottle 62, encloses, with the longitudinal axis thereof, an angle of 30 degrees with the horizontal line X.

The bottle 62 is placed on the sloped surface 61b of the mounting, and the position of the bottle is fixed from beneath by a support surface 61a perpendicular thereto. In this case, two resonators 68a, 68b are provided, one with the screen parallel to the sloped surface (68a), and the second perpendicular thereto under the bottle bottom (68b).

The identification of the bottle content, that is, the sample 63, is performed both through the lateral walls of the respective bottle and through the bottle bottom. The support surfaces 61a, 61b of the mounting for the bottle 62, beneath which the resonators are provided, are made of a material transparent to the evanescent microwave fields, for example they are made of Teflon.

The advantage of this arrangement 60 is that the resonator 68a provided under the sloped surface 61b of the mounting captures the maximum possible volume of the sample 63 when the bottles 62 are filled only partially, thereby contributing to increasing the accuracy and reproducibility of the measurement. In addition, the resonator 68b disposed under the bottle bottom is advantageously used to identify samples in bottles having a small diameter. In the case shown in FIG. 6, the angle between the sloped support surface 61b and the horizontal line X is 30 degrees. The resonators 68a, 68b are accommodated in the housing 66.

Second Embodiment

The measurements that are presently performed by a network analyzer could be implemented with an electronic circuit developed based on standard components for mobile communications and microelectronics. This would allow for the design of extremely compact and cost-effective testing devices.

The integration of such electronics and resonators into a housing serves as the prerequisite for the construction of so-called hand-held scanners. Such a hand-held scanner could be operated, for example, by means of rechargeable batteries and employed as a mobile device for the analysis of samples.

Third Embodiment

A further field of application is the determination of the water content in construction materials, for example to control the storage time of wood. The method could also be employed for analyzing packaged foods. In agriculture, the method could be employed for determining the water content in grains. In the field of medical applications, measurement of the water content of the skin (hydration) is conceivable.

Of course, the diameter of the opening in the metal housing must be optimized in each case for the oscillation mode that is used. The resonator is excited in an oscillation mode having low radiation loss.

It is conceivable that, for applications other than those described here, instead of the determination of the resonance frequency, the determination of the quality is sufficient to definitively identify the sample.

A method for identifying a sample in a container then comprises the following steps:
the container with the sample is disposed relative to a resonator,
a high-frequency signal is injected into the resonator in order to excite a resonant mode of the resonator,
the resonance curve of at least one resonant mode is measured, and
the sample is identified from the change in quality measured in comparison to a measurement without the sample container. A device according to the invention for identifying a sample in a sample container comprises at least one resonator and a mounting for a sample container, and further a first means for exciting a resonant mode of the at least one resonator, wherein the resonator and the mounting for the sample container can be disposed relative to one another such that, after exciting a resonant mode of the resonator, the resonant electric field of the resonator is able to penetrate a sample in a sample container at least partially, and further comprises a second means for measuring the resonance curve of the resonator changed by the sample. The device comprises a third means for determining the quality.

The invention claimed is:

1. A method for identifying a sample in a container comprising:
injecting a high frequency signal generated by a signal source to a resonator to excite at least one resonant mode of the resonator and measuring with a frequency measuring device a resonance frequency of the resonator without the container with the sample present in a high-frequency field of the resonator;
disposing the container with the sample proximate to the resonator;
injecting a high-frequency signal generated by the signal source into the resonator in order to excite a resonant mode of the resonator and determining with a measuring device a sample influenced resonance frequency of the resonator with the sample in the container penetrated by the high-frequency electromagnetic field of the resonant mode;
measuring with the measuring device a resonance curve of at least one resonant mode; and
determining a change in the sample influenced resonance frequency of the resonator in comparison with the measurement of the resonance frequency without the sample container in the high-frequency electromagnetic field and identifying the sample based on said change.

2. The method according to claim 1, further comprising determining with a frequency measuring device a quality factor of the resonance frequency.

3. The method according to claim 2, wherein a reciprocal quality factor is related to the sample influenced resonance frequency.

4. A method according to claim 1 wherein the sample is a liquid sample.

5. A method according to claim 1 wherein the sample is a solid sample.

6. A method according to claim 1 wherein the resonator is a dielectric resonator.

7. A method according to claim 1 wherein the resonant mode includes at least one of the group of a $TE_{01\delta}$ mode, further $TE_0$ modes and whispering gallery modes of the resonator.

8. A method according to claim 1 wherein:
the sample container is made of a material selected from the group of glass, plastic and ceramic; and
the material is with or without partial metallization, and with or without a label.

9. A method according to claim 1 wherein the sample container remains closed during the measurement.

10. A method according to claim 1, wherein the resonator is disposed in a metal housing and excited.

11. A method according to claim 1, wherein a metal housing is selected for the resonator, the housing having an opening so that the electromagnetic fields can penetrate into an exterior space relative and proximate to the housing.

12. A method according to claim 11 wherein the opening of the metal housing is oriented in a direction of the sample container.

13. A method according to claim 1, wherein in order to identify the sample, multiple measurements of the resonance curves are performed by the measuring device, in order to determine the change in resonance frequency, and optionally the quality of the resonator.

14. The method according to the claim 13, wherein the multiple measurements are performed with different distances from the sample to the resonator.

15. The method according to the claim 13, wherein the position of the resonator is shifted so as to change the distance from the sample container.

16. A method according to claim 15, wherein multiple measurements are performed, during which different resonant modes of a resonator are excited.

17. The method according to the claim 16, wherein definitiveness and selectivity during the identification are increased by determining the resonance frequency and quality of multiple modes.

18. A method according to claim 1, wherein resonant modes of more than one resonator are excited.

19. A method according to claim 1, wherein different resonant modes are excited in resonators having identical designs.

20. A method according to claim 1, wherein same resonant modes are excited in resonators not having identical designs.

21. A device for identifying a sample in a sample container, comprising:
   at least one resonator;
   a mounting device for a sample container;
   a signal source applied to excite a resonant mode of the at least one resonator;
   the resonator and the mounting device for the sample container being disposed relative to one another such that, after the resonant mode of the resonator is excited, a resonant electric field of the resonator penetrates the sample in the sample container at least partially
   a measuring device configured to measure a sample influenced resonance curve of the resonator changed by the sample and determine a change in the sample influenced resonance curve relative to a reference resonance curve measured without the sample present in the resonant electric field, and
   a frequency measuring device configured to measure a sample influenced resonance frequency of the resonant electric field with the sample disposed therein.

22. The device according to the claim 21, wherein the frequency measuring device is configured to determine a sample influenced quality factor of the resonator changed by the sample.

23. A device according to claim 22, wherein the frequency measuring device is configured to relate the sample influenced resonance frequency and the sampled influenced quality factor of the resonator to one another.

24. A device according to claim 23, wherein the frequency measuring device is configured to convert the sample influenced quality factor of the resonator, which was changed by the sample, into a reciprocal value thereof as a sample influenced reciprocal quality factor and relate the sample influenced reciprocal quality factor to the sample influenced resonance frequency.

25. A device according to claim 21, wherein the frequency measuring device is configured to present at least one of the following:
   the sample influenced resonance frequency, and a relationship between the sample influenced resonance frequency and the quality factor, or
   a relationship between the sample influenced resonance frequency and a reciprocal of a sample influenced quality factor as a function of a distance from the sample container to the resonator.

26. A device according to claim 25, wherein software configures the frequency measuring device.

27. A device according to claim 25, further comprising a positioning device configured to vary the distance from the sample container to the resonator.

28. A device according to claim 21 wherein the signal source is one of:
   a variable-frequency microwave oscillator, or
   a broadband amplifier having the resonator in a feedback circuit.

29. A device according to claim 21, wherein the frequency measuring device includes one of a detector diode, or a bolometric power detector, or a heterodyne receiver.

30. A device according to claim 21, wherein the frequency measuring device includes a network analyzer.

31. A device according to claim 21, wherein the resonator is disposed in a metal housing having at least one opening.

32. A device according to claim 31, wherein the opening of the metal housing is oriented toward the sample container and is permeable to electromagnetic fields of the resonator.

33. A device according to claim 31, wherein the resonator is disposed central-symmetrically in the metal housing.

34. A device according to claim 31, wherein the metal housing has a cylindrical shape.

35. A device according to claim 31, wherein circular cylindrical screen is the opening and is disposed centrally in the metal housing.

36. A device according to claim 21, wherein the mounting device for the sample container has at least two V-shaped grooves.

37. A device according to claim 21, wherein the resonator is a cylindrical dielectric resonator.

38. A device according to claim 21 wherein the container for the sample and a housing of the resonator are positioned relative to one another such that a lowest point of the container is disposed above and aligned with a center of an opening of the housing of the resonator.

39. A device according to claim 21, wherein the resonator includes multiple resonators arranged for receiving sample containers of different configurations.

40. A device according to claim 39, wherein the multiple resonators are disposed to correspond to a shape of the sample container.

41. A device according to claim 21 wherein the mounting device for the sample container is disposed such that a sample container disposed therein is disposed with a longitudinal axis thereof oblique to a horizontal axis.

42. The device according to the claim 41, wherein the sample container is disposed in the mounting device such that a longitudinal axis of the sample container assumes an angle of approximately 20 to 50 degrees with respect to the horizontal axis.

* * * * *